US009406096B2

(12) United States Patent
Bucolo et al.

(10) Patent No.: US 9,406,096 B2
(45) Date of Patent: Aug. 2, 2016

(54) METHOD FOR PREPARING A PATIENT FOR A MEDICAL TREATMENT

(75) Inventors: Salvatore Bucolo, Windsor (AU); Kate Sonia Miller, The Gap (AU); Emma Ann Uletta Paterson, Corinda (AU)

(73) Assignee: DTT (HOLDINGS) PTY LTD, Toowong, Queensland (AU)

( * ) Notice: Subject to any disclaimer, the term of this patent is extended or adjusted under 35 U.S.C. 154(b) by 1196 days.

(21) Appl. No.: 13/003,870

(22) PCT Filed: Jul. 14, 2009

(86) PCT No.: PCT/AU2009/000897
§ 371 (c)(1),
(2), (4) Date: Jul. 8, 2011

(87) PCT Pub. No.: WO2010/006362
PCT Pub. Date: Jan. 21, 2010

(65) Prior Publication Data
US 2011/0258570 A1    Oct. 20, 2011

(30) Foreign Application Priority Data
Jul. 15, 2008    (AU) .................................. 2008903628

(51) Int. Cl.
*G09B 5/00* (2006.01)
*G06Q 50/22* (2012.01)
(Continued)

(52) U.S. Cl.
CPC ............ *G06Q 50/22* (2013.01); *G06F 19/3437* (2013.01); *G06N 3/006* (2013.01); *G06Q 10/10* (2013.01); *G09B 5/00* (2013.01)

(58) Field of Classification Search
CPC ........... G06Q 10/10; G09B 5/00; G06N 3/006
USPC .......................................................... 715/771
See application file for complete search history.

(56) References Cited

U.S. PATENT DOCUMENTS

| 5,602,566 A | 2/1997 | Motosyuku et al. |
| 6,347,290 B1 | 2/2002 | Bartlett |

(Continued)

FOREIGN PATENT DOCUMENTS

| JP | 2003299879 | 10/2003 |
| WO | 99/18495 | 4/1999 |

(Continued)

OTHER PUBLICATIONS 2011-517713, Jan. 8, 2013, JP Office Action.

(Continued)

*Primary Examiner* — Jennifer To
*Assistant Examiner* — Ashley Fortino
(74) *Attorney, Agent, or Firm* — Workman Nydegger

(57) ABSTRACT

A method for using an electronic device having a display to prepare a patient for a medical treatment. The method includes the steps of representing a world on the display (300), wherein one or more medical objects related to the medical treatment are placed in the world; receiving an input from the patient to select the medical objects (326); selecting the medical objects; and providing feedback to the patient to indicate that the medical objects have been selected (327). The method reduces pain and anxiety when undergoing the medical treatment by familiarizing the patient with the medical objects, and by distracting the patient's attention from the treatment.

24 Claims, 14 Drawing Sheets

(51) Int. Cl.
  *G06N 3/00* (2006.01)
  *G06F 19/00* (2011.01)
  *G06Q 10/10* (2012.01)

(56) References Cited

U.S. PATENT DOCUMENTS

| | | | |
|---|---|---|---|
| 6,573,883 | B1 | 6/2003 | Bartlett |
| 6,918,769 | B2 | 7/2005 | Rink |
| 2001/0022719 | A1* | 9/2001 | Armitage et al. ............ 361/681 |
| 2003/0190950 | A1 | 10/2003 | Matsumoto |
| 2004/0002043 | A1* | 1/2004 | Dowrick ....................... 434/178 |
| 2004/0121295 | A1 | 6/2004 | Stuart et al. |
| 2006/0105825 | A1 | 5/2006 | Findlay |
| 2008/0097181 | A1 | 4/2008 | Brown |
| 2008/0225060 | A1* | 9/2008 | Thelen .......................... 345/676 |
| 2009/0027337 | A1* | 1/2009 | Hildreth ........................ 345/158 |
| 2009/0191529 | A1 | 7/2009 | Mozingo et al. |
| 2010/0157018 | A1* | 6/2010 | Lampotang et al. ............ 348/36 |

FOREIGN PATENT DOCUMENTS

| | | |
|---|---|---|
| WO | 03/025730 A1 | 3/2003 |
| WO | 2007/045021 A1 | 4/2007 |
| WO | WO2007/045021 | 4/2007 |
| WO | WO 2007045021 A1 * | 4/2007 |
| WO | 2010/060136 A1 | 6/2010 |

OTHER PUBLICATIONS

Office Action mailed Jun. 27, 2013 in CN 200980128004.5.
Stefan Marks et al: "Evaluation of Game Engines for Simulated Surgical Training", Dec. 1, 2007, pp. 273-318, XP007913237, Retrieved from the Internet @ http://www.cs.auckland.ac.nz/~stefan/documents/Stefan%20Marks%20-%20Graphite%202007%20-%20EvaluationGamesEngines.pdf.
09797260.8, Mar. 31, 2014, European Written Opinion.

* cited by examiner

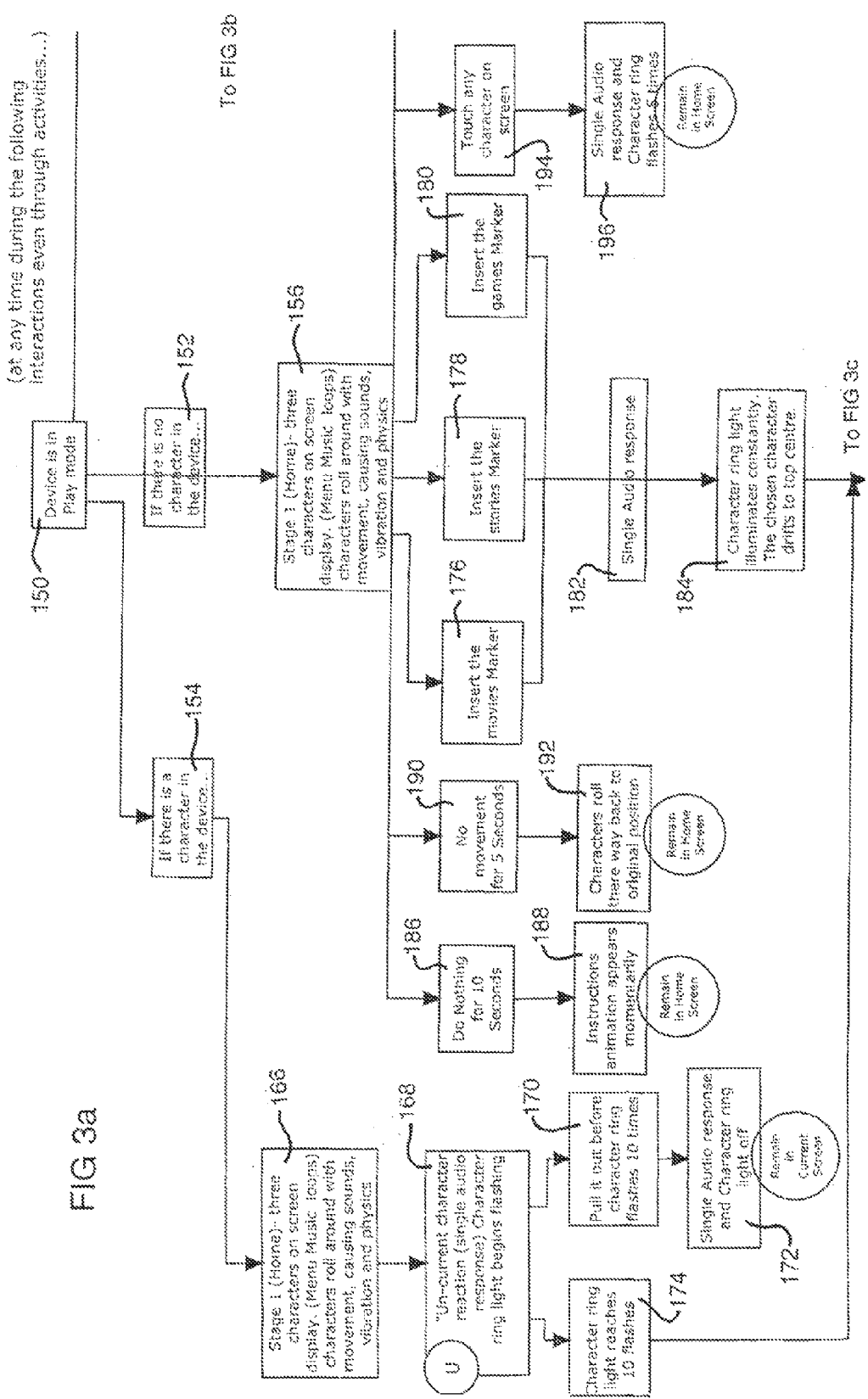

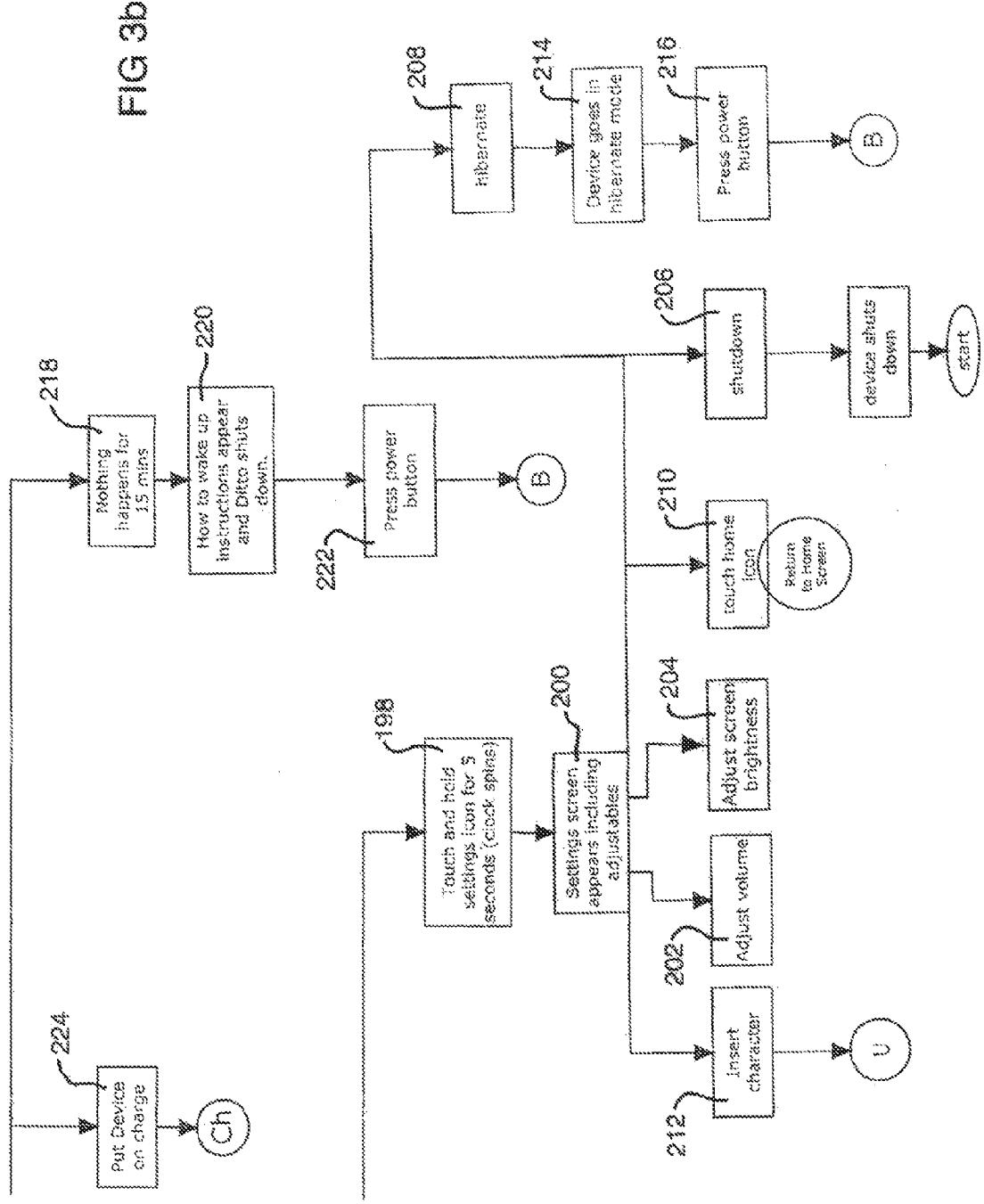

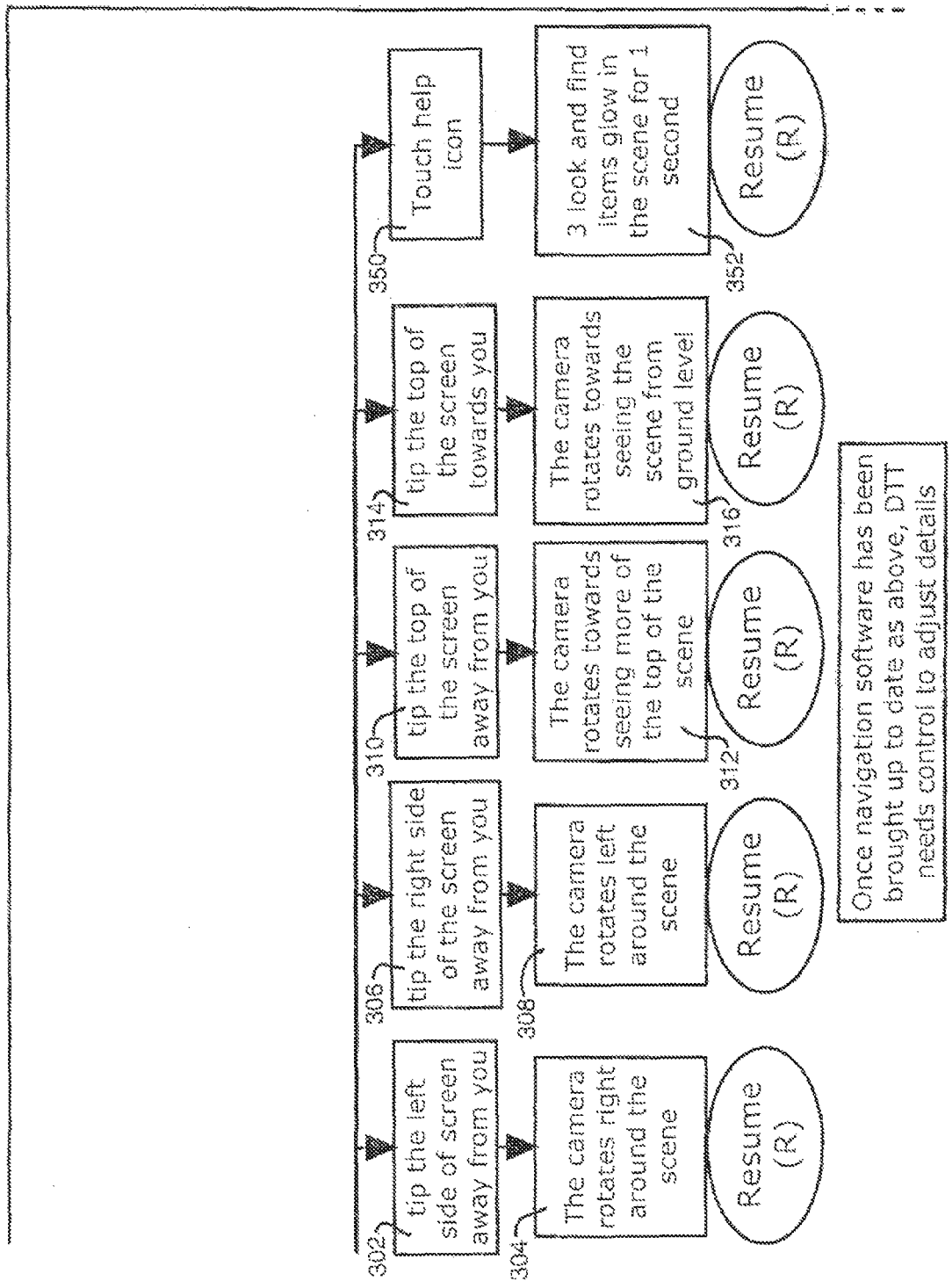

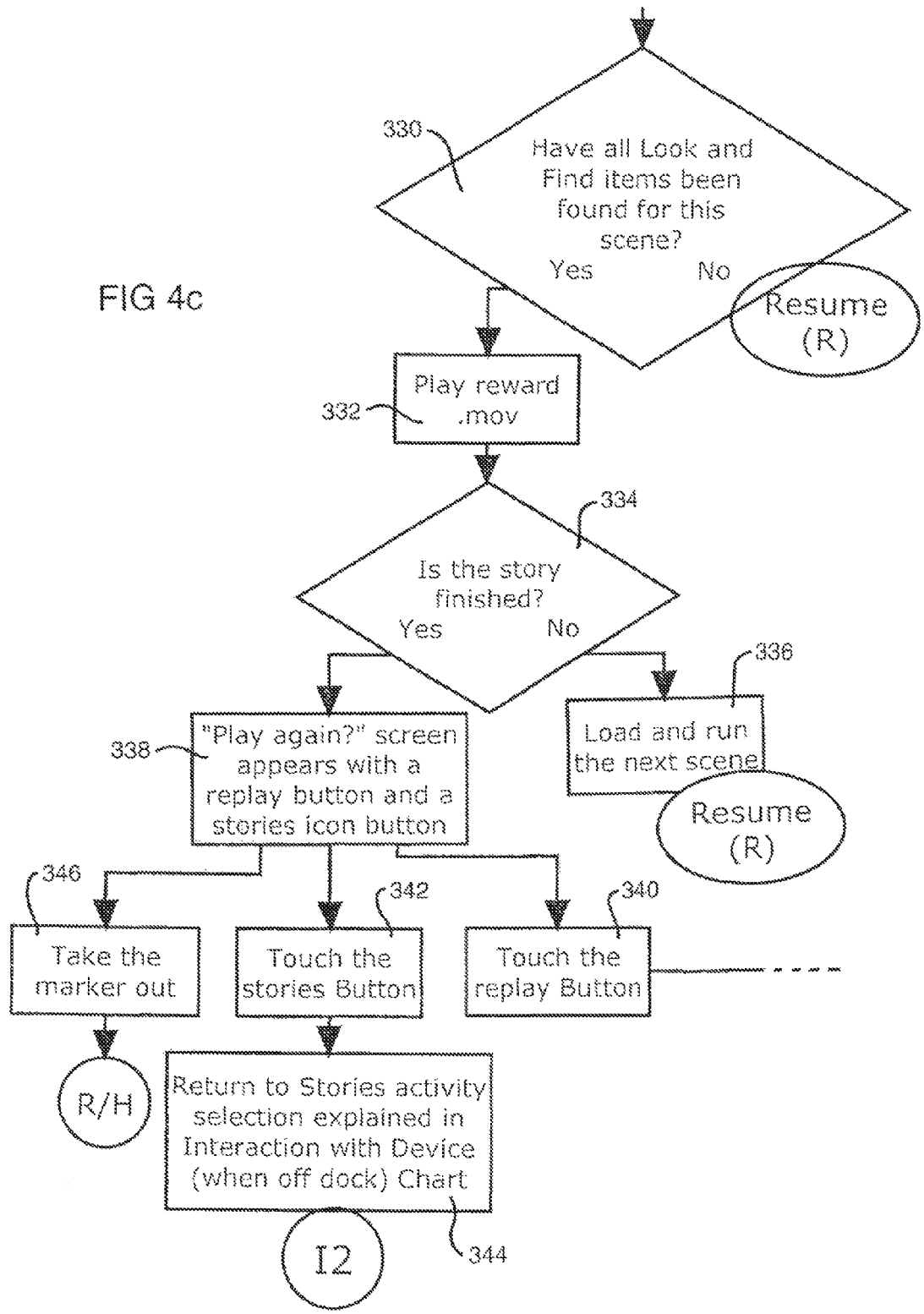

METHOD FOR PREPARING A PATIENT FOR A MEDICAL TREATMENT

TECHNICAL FIELD

The present invention relates to methods for preparing a patient for a medical treatment and electronic devices and computer programs for use in the preparation.

BACKGROUND

An important aspect of medical treatment is the management of pain and stress. Procedural preparation assists patients to understand and cope with medical procedures prior to experiencing them. Studies have shown that procedural preparation reduces patient anxiety, pain and distress levels and increases compliance with treatment procedures.

Currently, procedural preparation is carried out by therapists or nurses. It may involve discussions, educational stories, tours of treatment rooms and demonstrations on therapy dolls using actual medical equipment. Due to the intensive nature of most therapist run procedural preparation programs, not all patients receive preparation, particularly in outpatient settings where access to patients outside clinic time is rare.

It would therefore be desirable to provide an alternative method of preparing a patient for a medical treatment.

DISCLOSURE OF THE INVENTION

One aspect of the invention provides a method for using an electronic device having a display to prepare a patient for a medical treatment, the method including the steps of:

representing a world on the display, wherein one or more medical objects related to the medical treatment are placed in the world;

receiving an input from the patient to select the medical objects;

selecting the medical objects; and providing feedback to the patient to indicate that the medical objects have been selected.

The electronic device on which the method is performed could be a computer, a hand held video game console, a virtual reality system or any other electronic device having a display. An electronic device particularly suitable for use with the method is the tablet device described in International Patent application PCT/AU2006/001531, to the present Applicant, the entire contents of which are incorporated herein by reference. The display may take any suitable form, and may be for example a thin film transistor or like LCD screen.

The input from the patient could be via a keyboard, mouse, button, joystick, touch display, microphone or any other user input device. Similarly, the feedback to the patient could be provided via any output device, for example, the display, a speaker, earphones, vibration motor or light.

By familiarising the patient with the medical objects that they will encounter during a medical treatment, the present invention has been found by the Applicant to reduce patient pain and anxiety when undergoing the treatment using the medical objects. By way of illustration, the medical treatment could be in relation to a burn, and the medical objects may be bandages, scissors, creams and/or pills used in the treatment of the burn.

The present invention thus enables preparation for a medical treatment to be provided to patients without requiring therapist or nurse time. This frees the therapist or nurse to care for other patients, and may increase the number of patients who receive preparation for a medical treatment. The method may be used, for example, in the waiting room, by patients waiting to undergo a medical treatment.

Further, the method of the present invention may provide diversionary therapy to the patient by distracting the patient's attention so as to provide relief from pain and anxiety. The Applicant has found that immersive technology based distraction reduces both the emotional and sensory components of pain. The deeper the immersion, the more effective the analgesic properties.

The method may also include the step of representing one or more obscuring objects in the world, wherein one or more of the medical objects are obscured by one or more of the obscuring objects.

A medical object may be partially obscured by an obscuring object, or it may be wholly obscured, such that the patient cannot see the medical object. Obscuring objects could be, for example, tables, chairs, boxes or drawers. Representing one or more obscuring objects in the world may make the method even more immersive, by making it more difficult for the patient to identify and select the medical objects. This provides an additional distraction to the patient from the pain and anxiety associated with the medical procedure.

Further method steps may include receiving an input from a patient to perform at least one action to potentially reveal a medical object; and performing the action. The action could be moving the obscuring object. Tables or chairs, for example, may be lifted or moved in response to patient input. Alternatively or additionally, the action could be opening the obscuring object, if the obscuring object is a container object in which a medical object can be placed. Boxes or drawers, for example, may be opened in response to patient input to reveal one or more medical objects placed in them.

Alternatively or additionally the world may be three dimensional and the action could be changing the viewpoint of the world. The display may include a stereoscopic screen, so that the three dimensional world represented on the display appears to be in physical three dimensional space. Allowing the patient to change the viewpoint of a three dimensional world may further increase the immersiveness of the method. The patient may be required change the viewpoint of the world so as to look behind, underneath, on top of or inside obscuring objects in order to reveal the medical objects.

In one embodiment, the electronic device may include a motion sensor, and the viewpoint of the world may be changed in response to detecting motion of the electronic device from the motion sensor. This provides the patient with an interactive experience, and allows the patient to interact instinctively with the three dimensional world, for example through tilting or rotating the device. The motion sensor may take any form and could be, for example, an inertial measurement unit which may use gyroscopes and/or accelerometers. Alternatively, the viewpoint of the world may be changed in response to other patient inputs, such as pressing keys on a keyboard, clicking a mouse or button, moving a joystick, touching a touch display or speaking into a microphone.

The method may also include the steps of representing a character in the world; and moving the character within the world when selecting objects or performing actions on objects. The use of a character provides further distraction and may prolong the method, holding the attention of the patient for a longer period. A character such as a doctor, nurse, surgeon or therapist may be used, to familiarise the patient with the people who play a part in the medical treatment.

To further prolong the method and increase distraction, one or more non-medical objects that are not related to the medical treatment may be placed in the world, and the method may further include the steps of receiving an input from the patient to select the non-medical objects; selecting the non-medical objects; and providing feedback to the patient to indicate that the non-medical objects have been selected. For example, the non-medical objects may be balls, toys, drinks or any other object.

Feedback that can be provided to the patient when selecting the medical or non-medical objects may include playing a sound on a sound generator, such as a speaker or earphones, and/or indicating the objects on the display e.g. by causing them to increase in size. The sound played may depend on the object selected and, for example, sounds played when selecting non-medical objects may indicate that a special object or a wrong object has been selected. The feedback could also include vibrating a vibration motor, flashing a light, playing an animation or movie, or displaying images and/or text.

The method may further include representing images of the medical objects hidden in the world on an outer part of the display, and indicating via the image of the medical object on the outer part of the display whether or not the medical object has been selected. This allows the patient to see how many and which objects remain to be located. Images of the non-medical objects hidden in the world may also be represented on an outer part of the display with an indication of whether or not they have been selected.

The images of the objects on the outer part of the display may be represented in bubbles and the indication may be a symbol, such as a tick; and/or a change in colour of the image or the background of the image. For example, the images may appear in white bubbles, which are ticked when the image is selected. It will be appreciated that other ways of representing images of the objects and providing an indication are possible.

To provide assistance to patients using the method, the method may include the steps of representing a help object in the world; receiving an input from the patient to select the help object; and providing an indication of the location of the medical objects for a predetermined period of time when the help object is selected. The indication may be causing the medical objects to increase in size momentarily. The help object may be, for example, a question mark displayed in one corner of the display screen.

The electronic device may include a touch display and at least one input from the patient may be touching the touch display. Similarly to a motion sensor, a touch display allows the patient to interact instinctively with the three dimensional world. The touch display may take any suitable form, for example resistive, capacitive, infrared, surface wave acoustic or strain gauge. Of course, input from the patient may take other forms, such as those previously described.

The method may further include the step of displaying information explaining the medical treatment after all of the medical objects have been selected. This information could be a picture, text, a slide show, a sound, a movie and/or an animation. Characters represented in the world may take part in the explanation.

Displaying information explaining the medical treatment may further prepare the patient for the medical treatment and the people and medical instruments encountered during the treatment.

The method has application in many types of medical treatment, including in burns treatment, e.g. dressing of the burns, doing skin grafts, going to theatre, putting on a pressure garment. It is also applicable to other treatments in emergency medicine, oncology, radiology, dentistry and the like, e.g. removing IV drips, getting a blood test, having an ultrasound. It may be used with any age-groups, including adults, but is particularly useful for paediatrics care, and in younger children in the age ranges of 3 to 8.

The medical treatment may be one stage of a medical procedure including a number of medical treatments, and the method may further include repeating the steps of the method for at least one other, or for all of the medical treatment stages of the medical procedure.

For example, a burns patient may undergo a burns dressing change medical procedure which includes the following medical treatment stages: removing a dressing, consulting with a doctor, putting on a new dressing.

The method may be repeated for each medical treatment stage, with medical objects relevant to that stage placed in the same or a different world. It may take, for example, around 10-20 minutes to repeat the steps of the method for all of these treatment stages.

In the burns dressing change example, the stage of removing the dressing may prepare the patient for taking medication, getting onto the bed in the treatment room and holding their hand still so that the nurse can take off the dressing and clean the burn. It may prepare the patient for the nurse putting on gloves and using scissors to cut the bandages, applying a smelly water like solution to remove the tape. The patient may be given information about what their burn may look like, so that they do not feel stressed when seeing it for the first time. They may be prepared for pink water that is used to clean the burn.

After the method has been completed for this medical treatment stage, the method may then be repeated for the stages of consulting with a doctor and putting on a new dressing.

Any one or more of the methods described above may be performed by a computer program, which may be stored in the memory of the electronic device, for example a tablet device or a head mountable device. Other aspects of the invention extend to the computer program and the programmed electronic device.

Embodiments of the present invention will now be described, by way of example only, with reference to the accompanying drawings. It is to be understood that the particularity of the drawings does not supersede the generality of the preceding description of the invention.

DETAILED DESCRIPTION OF THE INVENTION

Figure 1:
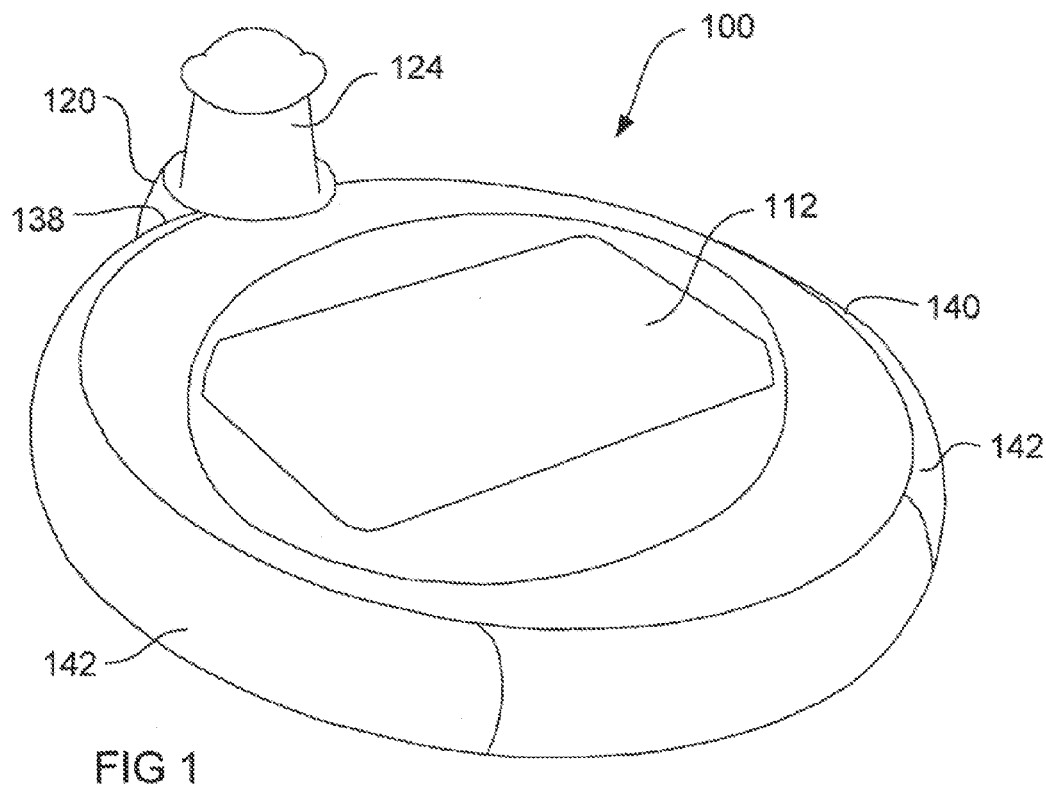
FIG. 1 is a side perspective view of a tablet device which can be used by embodiments of the invention.
Figure 2:
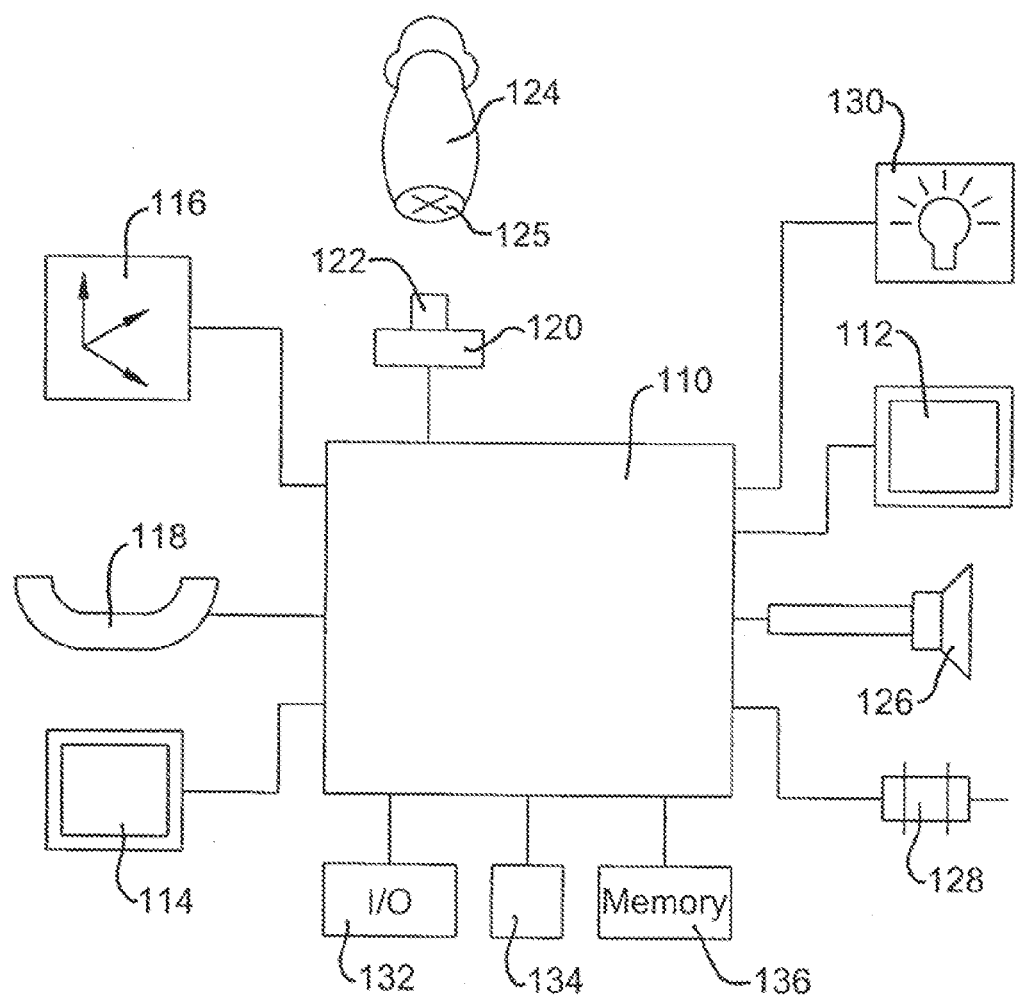
FIG. 2 is a block diagram of the tablet device of FIG. 1.

Referring to FIGS. 1 and 2, a tablet device 100 appropriate for use with the invention includes a controller 110 and a display screen 112. The controller 110 is configured to receive inputs from different user input devices on the tablet device 100 and to provide content to the display screen 112. The controller 110 may be a microprocessor or any other suitable processing element. It may be a single unit or may comprise a number of separate control units. The display screen 112 may be a LED screen or any other suitable screen.

The different user input devices on the tablet device 100 include a touch screen 114 and a motion sensor 116 which monitors the movement and position of the tablet device 100. The touch screen 114 may have soft buttons/activation regions and may be, for example resistive, capacitive, infrared, surface wave acoustic or strain gauge. The motion sensor 116 may be, for example, an inertial movement detector including gyroscopes and/or accelerometers.

Another input device on the tablet device 100 is a physiological sensor 118. The physiological sensor 118 may take a number of forms, and could measure heart rate, blood pressure, brain activity, muscle tension, skin conductivity, respiratory rates, oxygen saturation, general biometrics or the like. It could provide ECG, EEG or EMG information.

Another input device on the tablet device 100 is a socket 120 having an infrared detector 122. A selector element 124 having an infrared diode 125 may be placed into the socket 120, as shown in FIG. 1, and the controller 110 may, for example, use this input to make content and/or function choices. More than one selector element 124 may be used with the tablet device 100 to make different selections.

As well as providing content to the display screen 112, the controller 110 is also configured to provide other outputs via different output devices on the tablet device 100. Output devices on the tablet device 100 include a sound generator 126, which may be a speaker and/or earphones for providing audio outputs, a vibration motor 128 for providing haptic feedback and a light 130 that may be illuminated or flashed. The light 130 may be positioned around the socket 120.

Other input/output devices 132 on the tablet device 100 may include a link such as a wireless transceiver, network port or USB connection. This allows the controller 110 to download/upload content. The tablet device 100 is powered by rechargeable batteries 134 and includes a memory 136 accessible by the controller 110 for storing digital content, applications, operating systems and the like.

The tablet device 100 further includes a circular housing 138 with a dome shaped back. The shape of the back is particularly important in that it allows the user to manipulate the device supported on a surface with one hand or both hands bandaged. A hand grip area 140 is provided about the periphery of the housing 138, and a pair of main hand grips 142 are provided skew to the general horizontal axis of the device 100, e.g. as defined by the screen 112. The skew placement of the hand grips 148 prompts a user to rotate the device when picking it up.

The tablet device is suitably sealed to allow use in the bath as with many burns procedures and also to withstand the rigorous cleaning regime necessary to ensure infection control in a medical environment without ingress of cleaning or other liquids.

It will be appreciated that not all of these features will be necessary to perform the method of the invention and that a tablet device with a different combination of these features can be used. Also, the tablet device may have alternative or additional input/output devices, for example buttons, microphones and cameras. It will also be appreciated that the invention is not limited to using a tablet device and may also use a head mountable device or any other type of electronic device, including a computer, hand held video game console or virtual reality system.

Figure 3C:
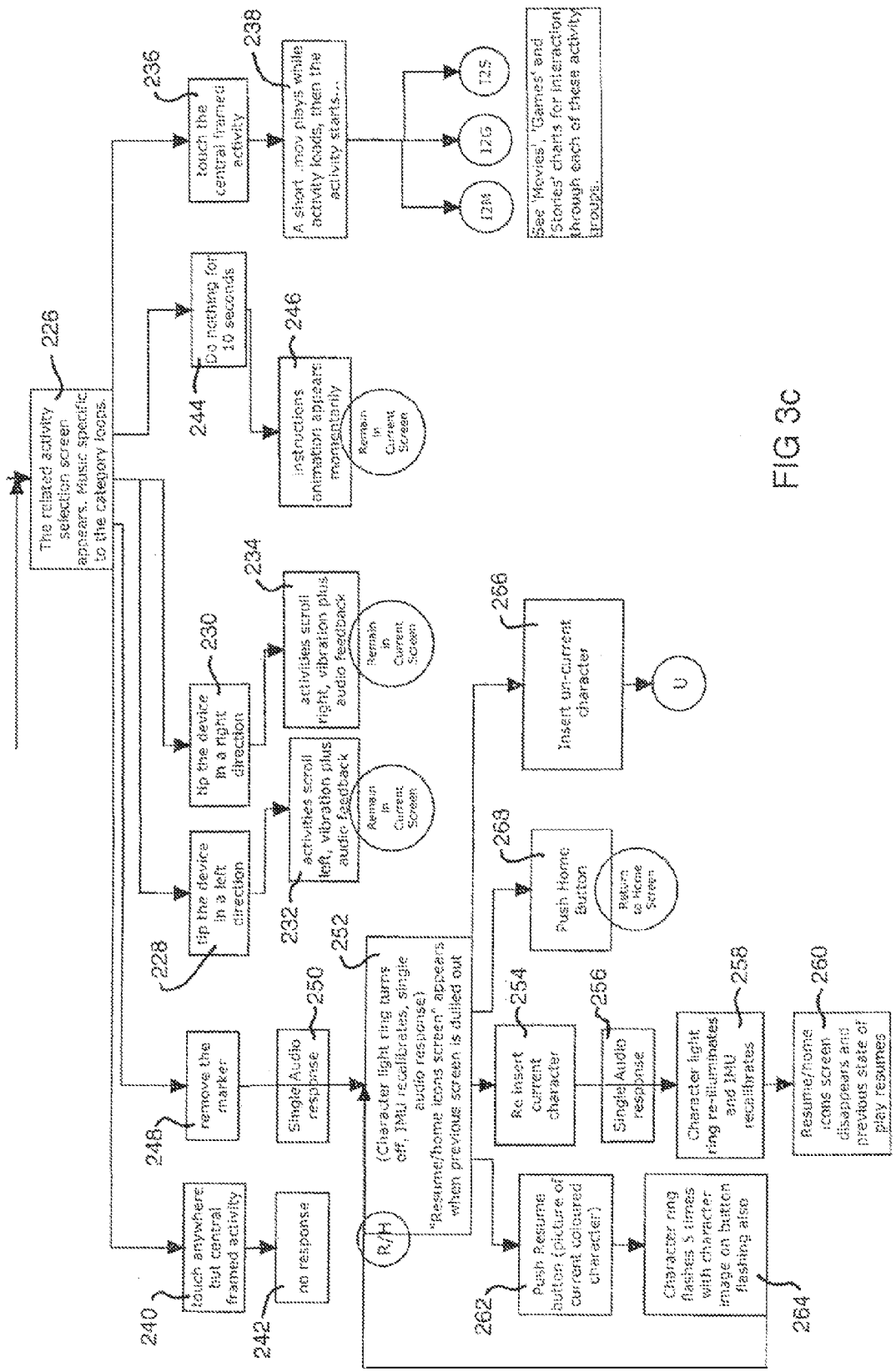
FIG. 3 is a flow chart of steps taken in the controller of the tablet device of FIG. 1 when a patient interacts with the device.

The tablet device 100 may be used by a patient before, during or after a medical treatment or procedure. A computer program stored in the memory 136 may include a series of instructions to cause the controller 110 to perform the steps shown in FIG. 3 when the patient interacts with the tablet device 100.

When the device is switched on at step 150 by pressing a power button, a load screen is represented on the display screen 112. The controller 110 then determines whether a selector element 124 is in the socket 120 at steps 152 and 154.

Figure 8:
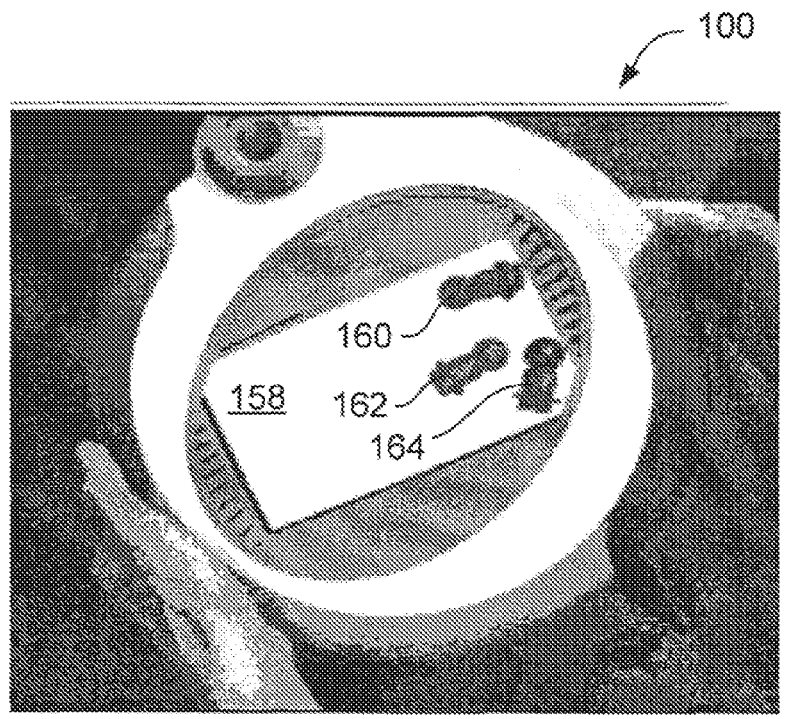
FIG. 8 is a front view of the tablet device of FIG. 1 displaying a home screen.

Whether or not there is a selector element 124 in the socket 120, a home screen 158, shown in FIG. 8, is represented on the display screen 112 at steps 156 and 166. This home screen includes three characters 160, 162, 164, coloured red, green and blue respectively, which roll around with movement of the tablet device 100 as monitored by the motion sensor 116. Sounds, and music play through the sound generator 126 and the vibration motor 128 vibrates.

If there is a selector element 124 in the socket 120, the controller 110 indicates that there is an "un-current reaction" at step 168 by providing a single audio response on the sound generator 126 and flashing the light 136. If the selector element 124 is pulled out before 10 flashes of the light at step 170, an audio response is played on the sound generator 126 and the flashing ceases at step 172. If the light 130 is flashed 10 times without action being taken, the controller 110 takes this as being a selection associated with the selector element 124 at step 174.

Figure 9:
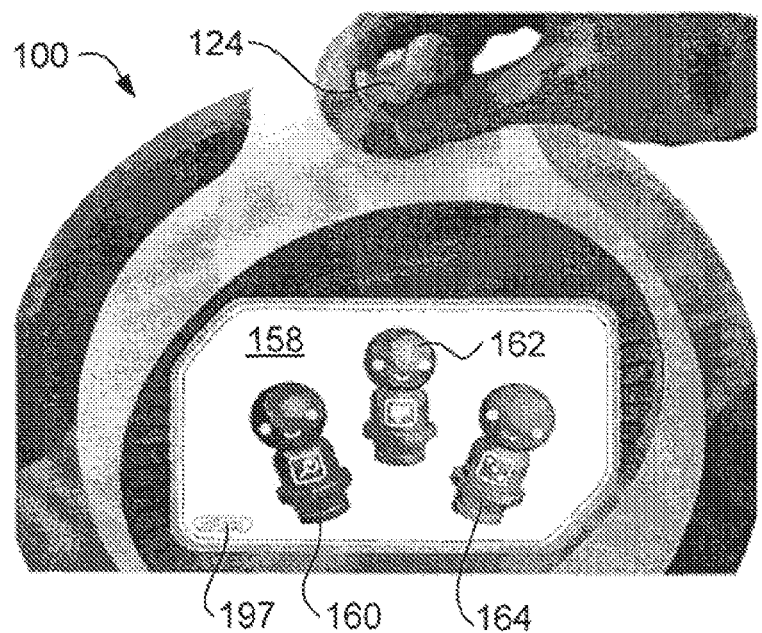
FIG. 9 is a front view of the tablet device of FIG. 1 with a selector element being inserted into the device.

If there is no selector element 124 in the socket 120, the patient may select an activity type from the group: movies, stories and games at steps 176, 178 or 180 by inserting an appropriate selector element 128. This is illustrated in FIG. 9. There may be three selector elements, coloured red, green and blue, which correspond to the characters 160, 162 and 164 on the home screen. Each selector element/character is associated with one of the three activity types. The controller 110 acknowledges the selection with a single audio response at step 182 and illuminates the light 130 constantly at step 184. The character 160, 162 or 164 associated with the selection drifts to the top of the display screen 112.

If the patient does not make a selection within 10 seconds by inserting a selector element 124 in the socket 120, at steps 186 and 188 an instruction animation appears on the display screen 112 momentarily. If the motion sensor 116 detects no movement of the tablet device 100 for five seconds at step 190, the characters 160, 162 and 164 move to a default position on the display screen 112 at step 192.

The patient may touch the touch screen 114 at the position of a character 160, 162 or 164 at step 194. The controller 110 then plays a single audio response on the sound generator 126 and flashes the light 130 five times at step 196.

A settings icon 197, as illustrated in FIG. 9, may also be represented on the screen 112, and the patient may touch and hold the settings icon for five seconds at step 198. In response to this, the controller 110 causes a clock to be displayed with spinning hands and a settings screen to be represented on the display screen 112 at step 200. The settings screen may include a battery life indicator, and icons allowing different functions to be performed including adjusting volume at step 204, adjusting screen brightness at step 204, shutting down the device at steps 206 and 207 and hibernating the device at step 208. Touching a home icon at step 210 returns the patient to the home screen, and inserting a selector element 118 at step 212 causes the controller to indicate that there is an "un-current reaction" as described above.

The device may or may not have a hibernation option. If the hibernation option is available, hibernating the device 100 causes the display screen 112 to be turned off at step 214. The display screen 112 can then be turned back on by pressing the power button at step 216. This causes the load screen to be displayed. If the hibernation option is available, any time that the device 100 receives no input for 15 minutes, it automatically goes into hibernation at steps 218, 220 and 222. Also, the device 100 may be put onto a charger at step 224 to recharge the battery 134 at any time. A warning may be displayed on the display screen 112 to indicate that the battery 134 needs charging. For example, a warning may be displayed when the battery life is 15% or less.

After the patient has made a selection using a selector element 128, at step 226 an activity screen related to the selection is represented on the display screen 112 and music specific to the selection is played on the sound generator 126. For example, a stories screen may be displayed. The patient may then tip the device right or left at steps 228 and 230 to scroll through different activities that may be chosen by touching the touch screen 114. At the same time, the controller 110 causes the vibration motor 128 to vibrate and audio feedback to be played on the sound generator 126.

The patient may use the touch screen 114 to choose an activity at step 236. The controller 110 causes a short movie to be played while the activity loads at step 238.

If the patient touches the touch screen 114 in an area that is not associated with an activity at step 240, no response is provided at step 242. If no input is provided for ten seconds at step 224, then an instruction animation appears momentarily on the display screen 112.

If the patient removes the selector element 124 from the socket 120 at step 248 then the controller 110 causes a single audio response to be played on the sound generator 126 at step 250. At step 252 the activity screen fades and a resume screen appears. The motion sensor 116 recalibrates and the light 130 turns off.

The patient may return to the previous activities screen by re inserting the selector element 124 at step 254. The controller 110 then causes a single audio response to be played on the sound generator 126 at step 256, the light 130 to re-illuminate, the motion sensor 116 to recalibrate at step 258 and the resume screen to disappear and the previous activity screen to re-appear on the display screen 112 at step 260.

If the patient instead touches a resume button on the resume screen at step 262, the light 130 and an image of a character on the resume button, having a colour corresponding to the activity type selection, flash five times at step 264. This is a prompt for the patient to re-insert the selector element 128.

If the patient inserts a different selector element 124 at step 266 this causes the controller 110 to indicate that there is an "un-current reaction" as described above. Alternatively, the patient may push a home button on the resume screen at step 268, which causes the controller 110 to represent the home screen 158 on the display screen 112.

Figure 4A:
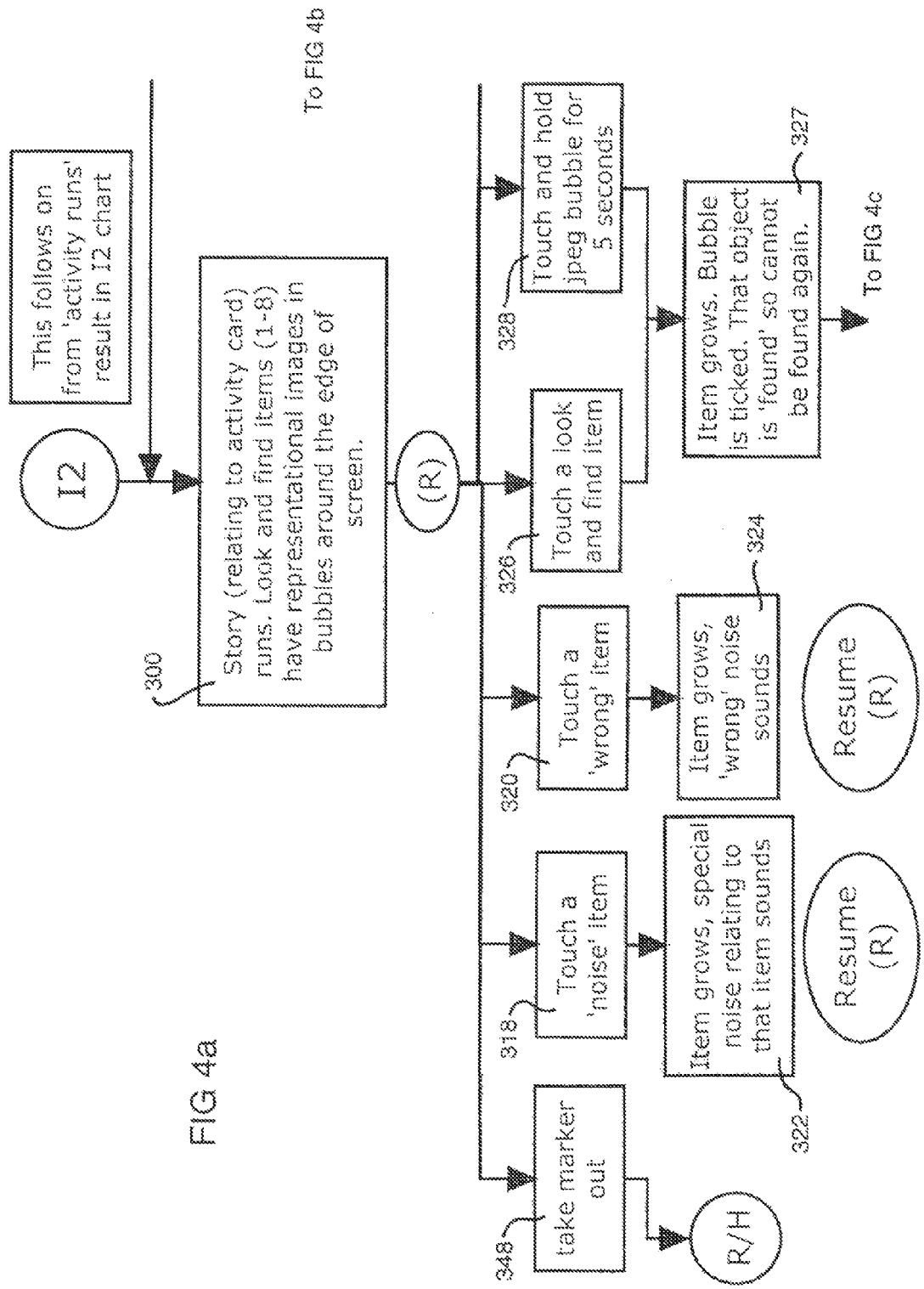
FIG. 4 is a flow chart of steps taken in the controller of the tablet device of FIG. 1 for preparing a patient for a medical treatment in accordance with an embodiment of the invention.

FIG. 4 shows the steps taken in the controller when the patient chooses a stories activity at step 236. A stories activity is a look and find activity related to a medical treatment and involves the controller 110 representing a world on the display screen 112, wherein one or more medical objects related to the medical treatment are placed in the world. The controller 110 then receives an input from the patient to select the medical objects, selects the medical objects and provides feedback to the patient to indicate this selection.

Figure 5:
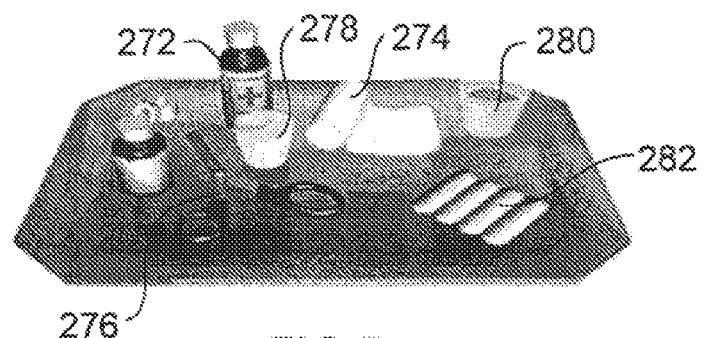
FIG. 5 is a perspective view of medical objects.
Figure 6:
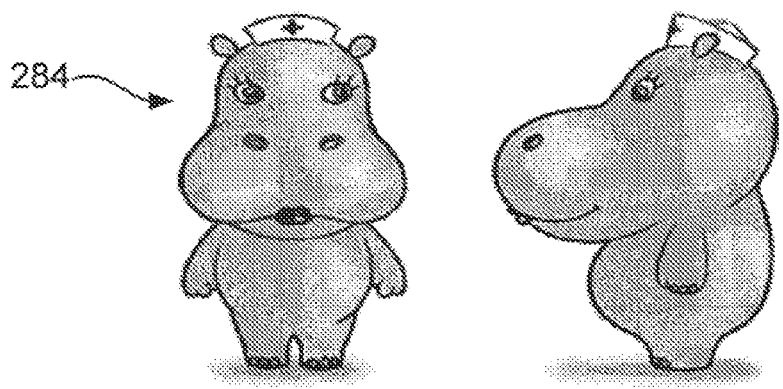
FIG. 6 is a front and side view of a character.
Figure 7:
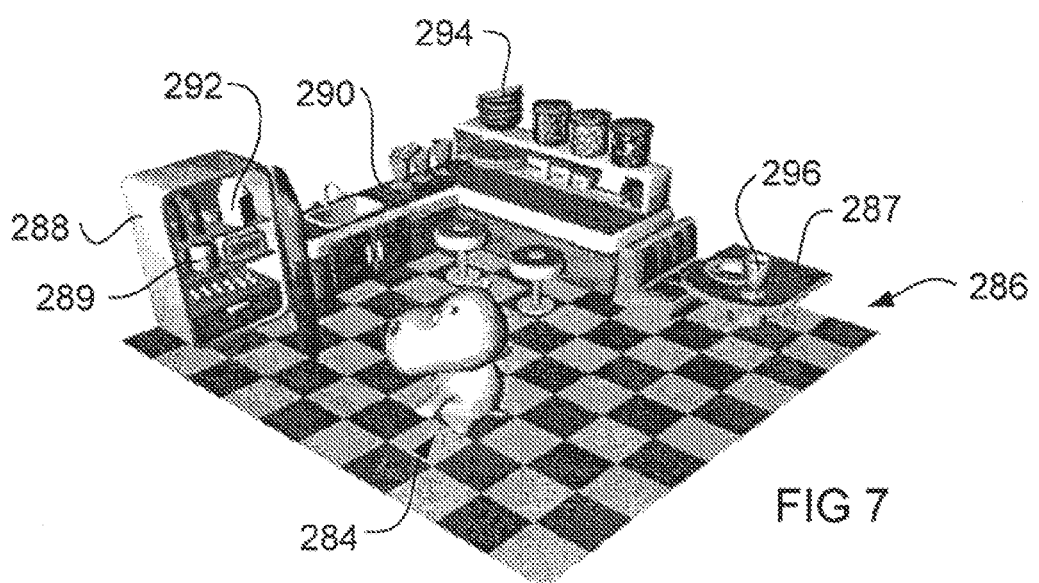
FIG. 7 is a perspective view of a three dimensional world.

FIGS. 5 to 7 show graphics that can be used in a stories activity. In FIG. 5 medical objects, including medicine bottles 270 and 272, bandages 274, scissors 276, empty and full medicine cups 278 and 280 and pills 182 are illustrated. FIG. 6 shows a character 284 from front and side perspectives. In FIG. 7 a three dimensional world 286 is represented, with the character 284 positioned in the world 286. The world 286 has obscuring objects including a table 287 and a box 289, container objects including a fridge 288 and a cupboard 290 and many non-medical objects, including for example a carton 292, plates 294 and a drink 296.

Referring now to FIG. 4, the selected stories activity is run at step 300 and images of the look and find objects 298, 299 and 301 to be found are represented on the outer part of the display screen 112 in bubbles. The look and find objects 298, 299 and 301 may include medical objects 270-282 and non-medical objects 292-296. The medical objects 270-282 are placed in the world 286, some are obscured by obscuring objects 287, 289 and some by container objects 288, 290.

The patient may then move the device 100 or touch the touch screen 114 to perform an action to potentially reveal the look and find objects 298, 299 and 301.

In the case of movement, the controller 110 detects the motion of the device 100 from the motion sensor 116 and changes the viewpoint of the world 286 in response to this motion. This allows the patient to look behind objects in the world 286.

If the device 100 is tipped left at step 302, the viewpoint rotates right around the world 286 at step 304. If the device 100 is tipped right at step 306, the viewpoint rotates left around the world 286 at step 308. If the top of the device is tipped away from the patient at step 310, the viewpoint moves downwards at step 312. If the top of the device is tipped towards the patient at step 314, the viewpoint moves upwards at step 316.

Figure 10:
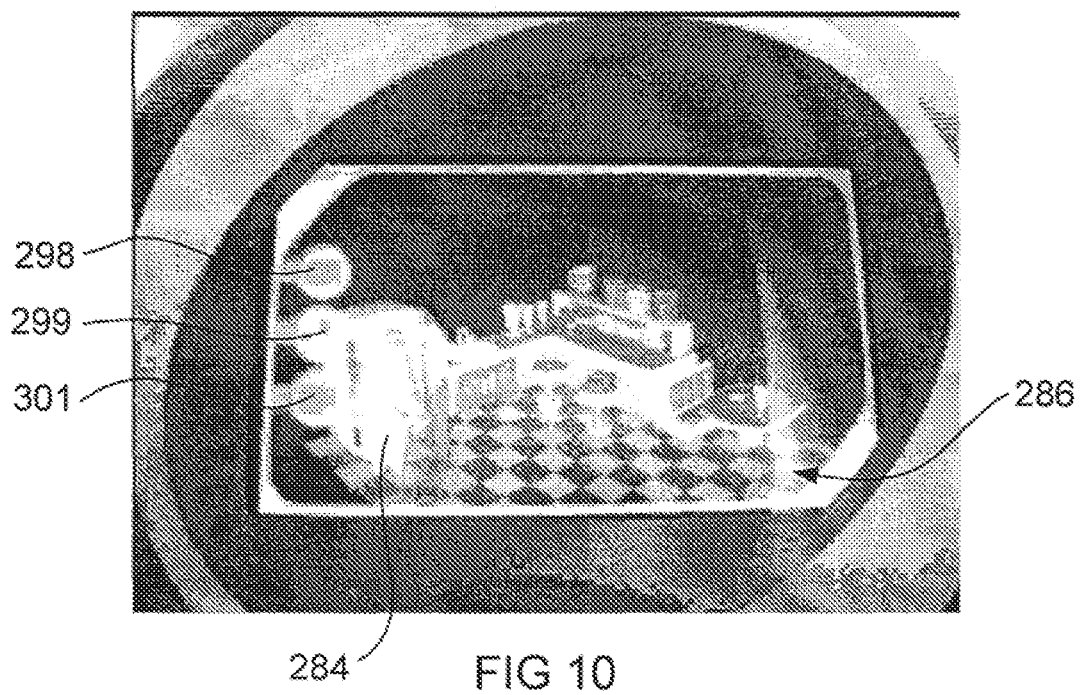
FIG. 10 is a front view of the tablet device of FIG. 1 displaying a three dimensional world at a first point in time.
Figure 11:
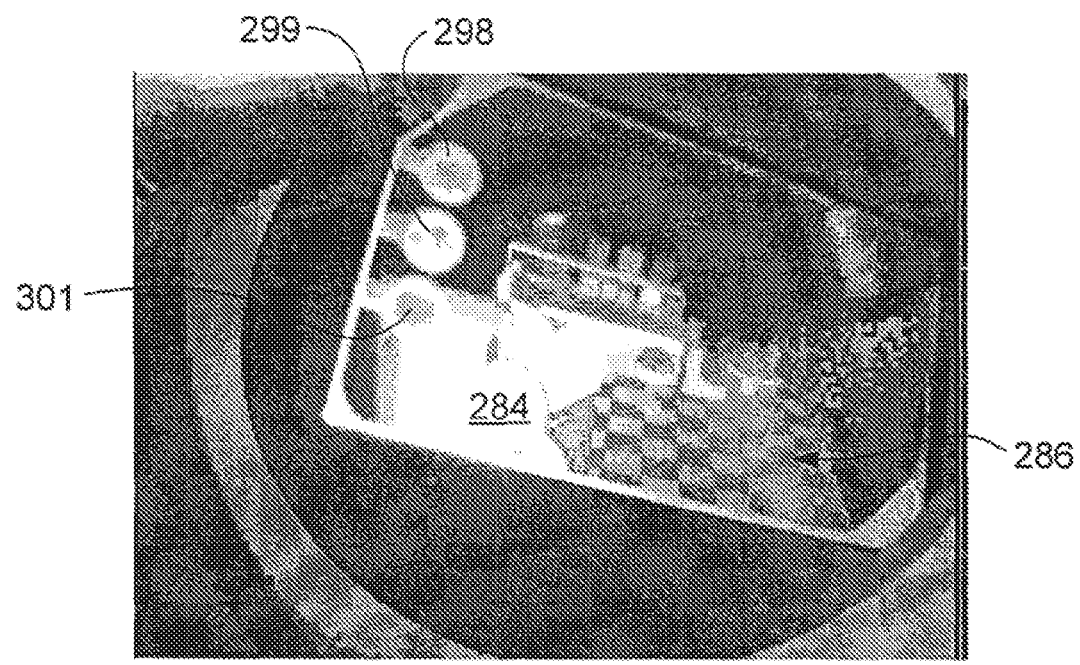
FIG. 11 is the view of FIG. 10 at a second point in time.
Figure 12:
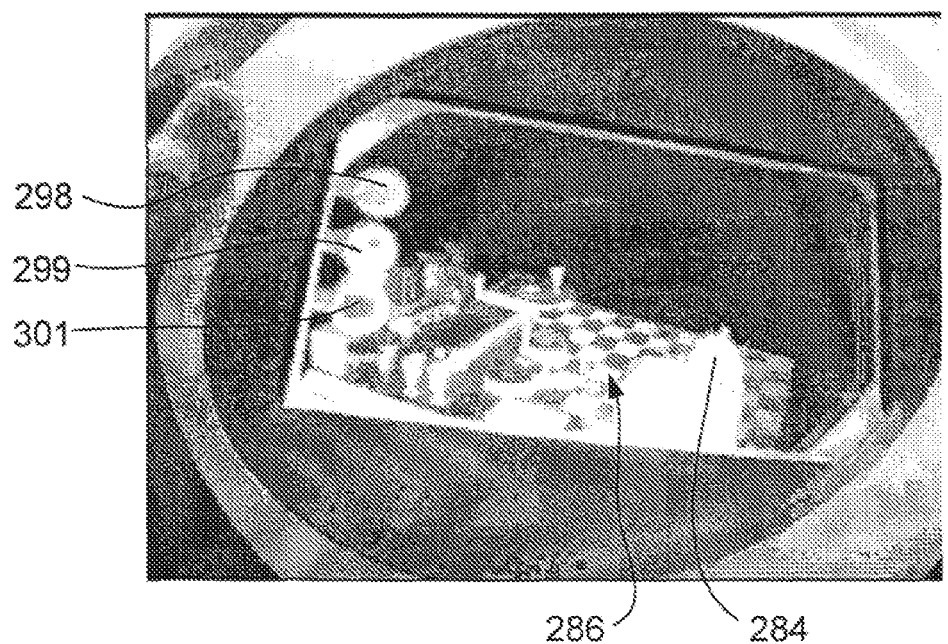
FIG. 12 is the view of FIG. 10 at a third point in time.

FIGS. 10 to 12 show the device 100 and the content represented on the display screen 112 at three different points in time. At the first point in time, shown in FIG. 10, the device 100 is held steady. The device 100 is then tipped right and the top tipped towards the patient at the second point in time. This moves the viewpoint left and upwards as seen in FIG. 11. The device is then held in this position, and at the third point in time, the viewpoint has rotated further left around the world 286 and further upwards as seen in FIG. 12.

Figure 13:
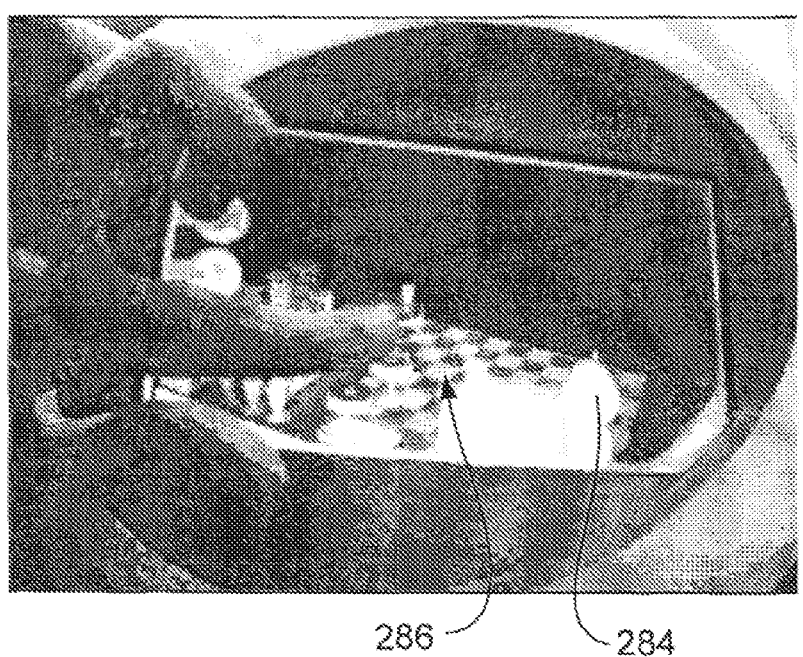
FIG. 13 is the view of FIG. 10 at a fourth point in time.

Other actions may be performed on objects by touching their images on the touch screen 114. For example, touching the container objects 288, 290 may cause them to open and touching the obscuring objects 287, 289 may cause them to move. This potentially reveals look and find objects 298, 299 and 301 hidden inside or behind these objects. FIG. 13 shows a patient touching an object in the world 286.

The character 284 represented in the world 286 may be moved within the world 286 when selecting objects or performing actions on objects. For example, when the patient touches the position on the touch screen 114 corresponding to the image of the fridge 289, the character 284 may walk to the fridge 289 and open it.

Some objects may be designated "noise" objects or "wrong" objects. If these objects are touched at steps 318 and 320, they increase in size for half a second, or the time that they are touched and then shrink to their normal size and a noise relating to the object is played on the sound generator 126 at steps 322 and 324. The same noise may be played for each "wrong" object that is touched and different noises may be played for each "noise" object.

Figure 14:
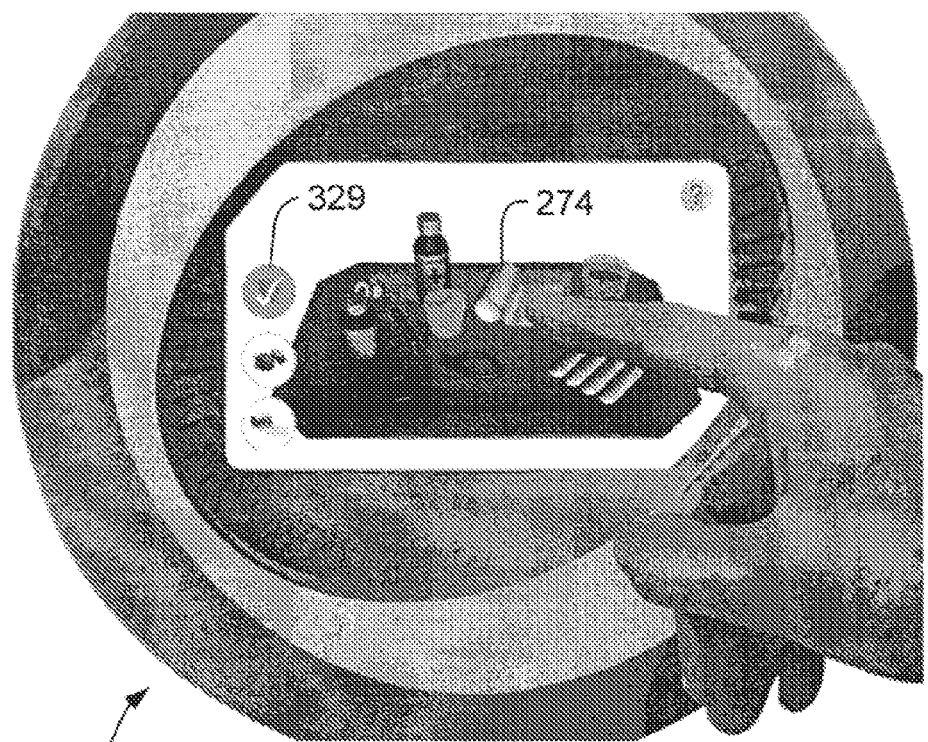
FIG. 14 is a front view of the tablet device of FIG. 1 showing a medical object being selected.

If a look and find object 298, 299 and 301 is touched at step 326, at step 327 the controller 110 causes the object to increase in size for one second and then shrink to its normal size and a sound plays on the sound generator 126. FIG. 14 shows a medical object 274 being selected. The controller 110 indicates via a tick 329 on the image of the object in a bubble on the outer part of the display that the object has been selected. The object cannot be selected by the patient again. The controller 110 may also perform the actions of step 327 if the image of the object in the bubble is touched and held for 5 seconds at step 328.

Figure 15:
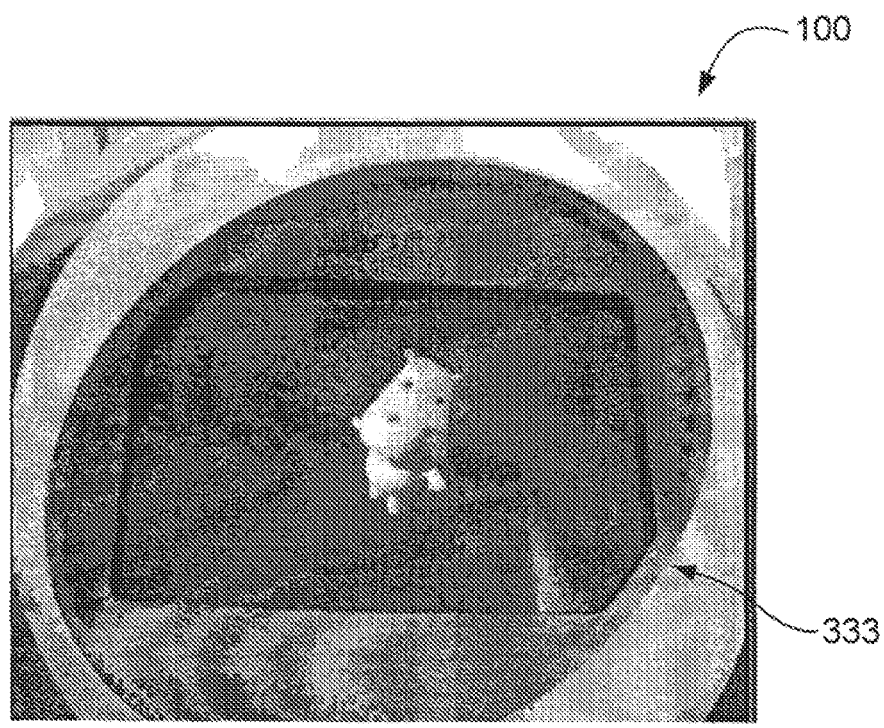
FIG. 15 is a front view of the tablet device of FIG. 1 displaying a reward movie.

Once the controller 110 determines that all of the look and find objects 298, 299 and 301 have been selected at step 330, a reward movie is played at step 332. An example of a scene 333 from a reward movie is shown in FIG. 15. The reward movie may explain the medical treatment. Alternatively, other information such as a picture, text, slide show, sound or animation explaining the medical treatment may be shown.

The stories activity may include multiple chapters, with each chapter relating to a different medical treatment stage of a medical procedure. For example, a burns dressing change story may include chapters for the following medical treatment stages: removing a dressing, consulting with a doctor, putting on a new dressing.

There may be chapters for all stages of a medical procedure. After all of the look and find objects 298, 299 and 301 in one stage have been selected, the controller 110 determines at step 334 whether the story is finished. If not, it loads and runs the next chapter of the story at step 336. If the story is finished, a play again screen is represented on the display screen 112 at step 338, with a replay button and a stories button. Touching the replay button at step 340 causes the stories activity to reset. Touching the stories button at step 342 causes the stories screen to appear at step 344 and the actions described above in relation to the stories screen apply.

If the selector element 124 is taken out of the socket 120 during the stories activity at step 346 or 348, the resume screen appears and the actions described above with reference to the resume screen apply.

Figure 17:
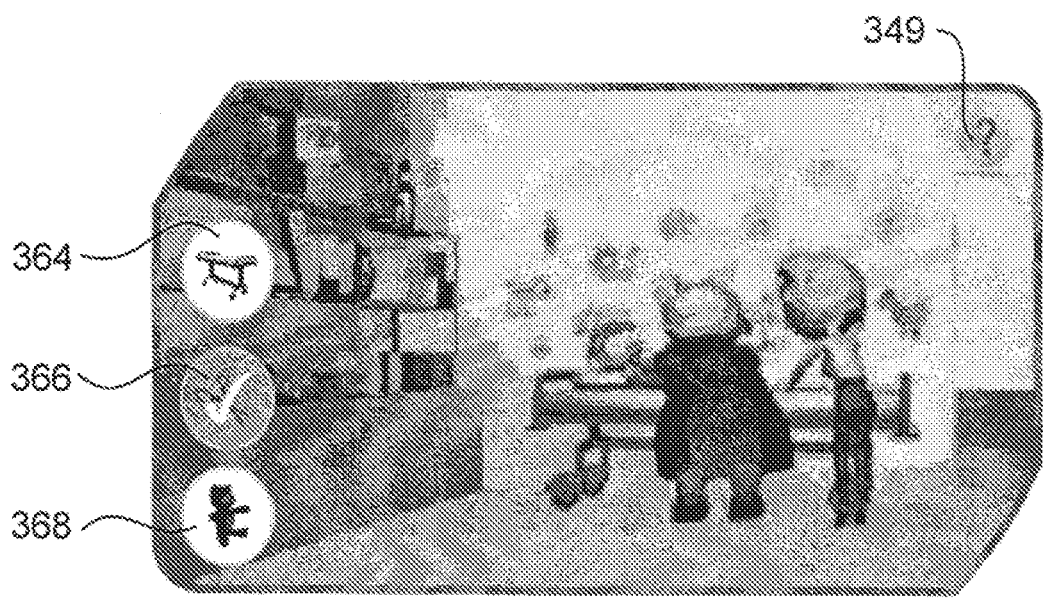
FIG. 17 is a front view of the tablet device of FIG. 1 displaying an alternate three dimensional world based on the procedural preparation story of FIG. 16.

A help object 349 may also be represented in the world 286, for example as shown in FIG. 17. The patient may touch the touch display 114 on the image of the help object 349 at step 350 causing the controller 110 to cause the look and find objects 298, 299 and 301 to grow in size for 3 seconds, or any other predetermined period of time at step 352.

The method may be used, for example, to prepare a child with burns for a dressing change. It is common for a burns patient to require multiple dressing changes over the period from injury to healing, which can be up to 12 weeks. Dressing changes can be painful and anxiety provoking, and the short and long term consequences of repeated painful procedures are concerning.

Preparing a child for a dressing change may provide relief from anxiety and relieve any misconceptions the child may have. For example, the child may be taught what the nurses do and why, which parts of the procedure may hurt, what the treatment room looks like and what the medical instruments look like and how they work.

Figure 16:
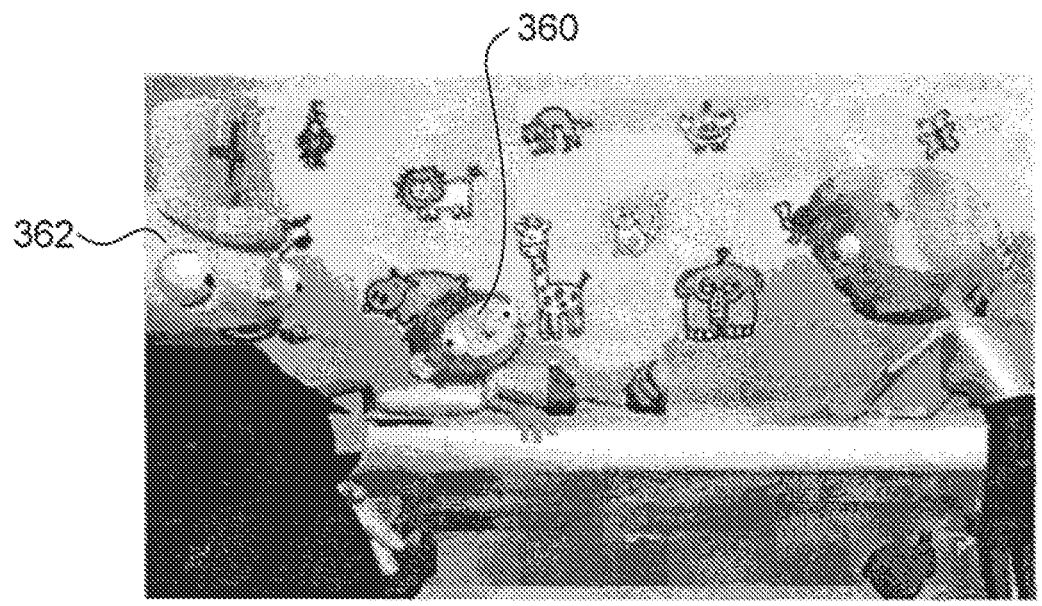
FIG. 16 is a front view of the tablet device of FIG. 1 displaying a scene from a procedural preparation story.

FIG. 16 shows a scene from a procedural preparation story that teaches a child how to ask for a pause from medical treatment. This may give the child a sense of control when undergoing the dressing change. In this scene, a character 360 called Bobby is depicted as undergoing a dressing change. Bobby 360 is shown asking for a break or pause in medical treatment and the nurse 362 instructs him to find three objects 364, 366 and 368 hidden in the room. The child is then asked to help Bobby 360 by locating and touching the hidden objects 364, 366 and 368 in the three dimensional world shown in FIG. 17. When they have done this the nurse 362 is depicted as resuming the dressing change on Bobby 360.

Different stories may be used to teach the child about different aspects of the medical treatment.

Figure 18:
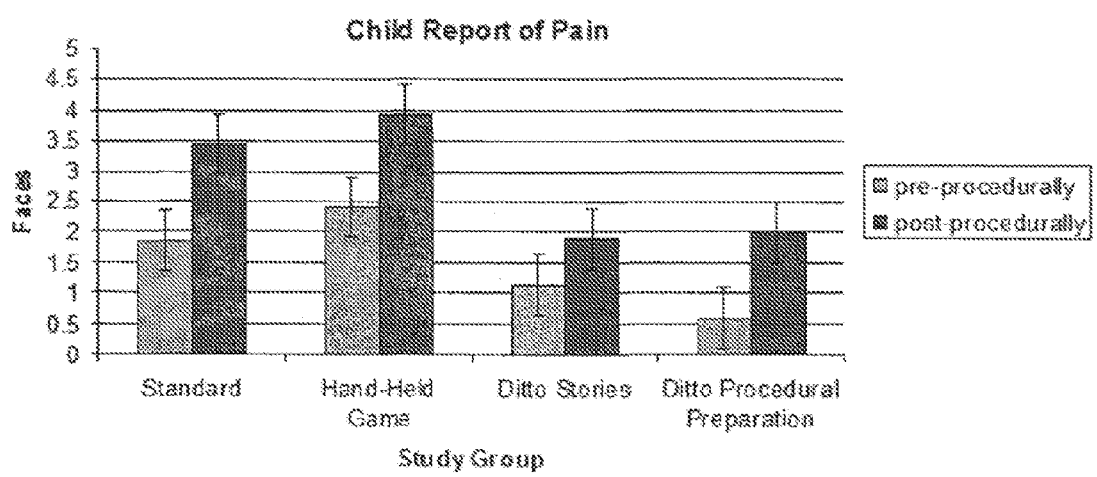
FIG. 18 is a graph of children's pre and post procedurally reported levels of pain for different study groups.

The Applicant has found that procedural preparation in accordance with the method described above assists in lowering pre-procedural pain scores (keeping the child calm and happy before the procedure begins) and also continues to assist with pain, anxiety and distress levels throughout the entire procedure. The Applicant has found that most children will refer to Bobby during the procedure and let the nurses know if they are not doing things correctly. This feedback shows that children are not only listening and interacting but also learning from this type of procedural preparation, and then using it in the real situation. FIG. 18 shows a preliminary graph that indicates that children's pre and post procedural pain scores using the procedural preparation method described above are less compared to standard distraction and hand held video games.

It is to be understood that various alterations, additions and/or modifications may be made to the parts previously described without departing from the ambit of the present invention, and that, in light of the above teachings, the present invention may be implemented in software, firmware and/or hardware in a variety of manners as would be understood by the skilled person.

The invention claimed is:

1. A method for using an electronic device having a display to prepare a patient for a medical treatment, the method including the steps of:

representing a world on the display, wherein one or more medical objects related to the medical treatment the patient is preparing to receive are placed in the world represented on the display;

representing one or more obscuring objects in the world, wherein one or more of the medical objects related to the medical treatment are at least partially obscured by one or more of the obscuring objects;

receiving a first input from a patient to perform at least one action to reveal a medical object in the world represented on the display that is at least partially obscured by an obscuring object and performing the action;

receiving a second input from the patient to select the medical object once the medical object used in the medical treatment is revealed in the world represented on the display and selecting the medical object;

providing feedback to the patient to indicate that the medical object has been selected; and presenting information on the display to explain to the patient the medical treatment to which the one or more selected medical objects relate;

wherein the world is three dimensional and the electronic device includes a motion sensor for detecting motion of the electronic device corresponding to the first input which is received by the motion sensor;

wherein the at least one action performed includes moving the obscuring object represented in the world or changing the viewpoint of the world represented on the display in response to the first input received by the motion sensor, to reveal the medical object in the world that has been at least partially obscured by an obscuring object, for selection of the revealed medical object when the second input is received from the patient.

2. The method according to claim 1, wherein the obscuring object is a container object in which a medical object can be placed, and the action includes opening the container object.

3. The method according to claim 1, further including the steps of:
representing a character in the world; and
moving the character within the world when selecting a medical or obscuring object or performing an action on a medical or obscuring object.

4. The method according to claim 1, wherein the electronic device includes a speaker and providing feedback includes:
playing a sound on the speaker when selecting the medical objects.

5. The method according to claim 1, wherein providing feedback includes:
causing the medical objects on the display to increase in size when selecting them.

6. The method according to claim 1, wherein providing feedback includes;
vibrating via activation of vibration motors.

7. The method according to claim 1, further including the step of:
representing images of the medical objects hidden in the world on an outer part of the display.

8. The method according to claim 7, further including the step of:
indicating via the image of the medical object on the outer part of the display whether or not the medical object has been selected.

9. The method according to claim 1, wherein one or more non-medical objects that are not related to the medical treatment are placed in the world, further including the step of:
receiving an input from the patient to select the non-medical objects;
selecting the non-medical objects; and
providing feedback to the patient to indicate that the non-medical objects have been selected.

10. The method according to claim 9, wherein providing feedback to indicate that the non-medical objects have been selected includes:
playing a sound on the speaker when selecting the non-medical objects.

11. The method according to claim 10, wherein the sound played depends on the non-medical object selected.

12. The method according to claim 9, wherein providing feedback to indicate that the non-medical objects have been selected includes:
causing the non-medical objects on the display to increase in size when selecting them.

13. The method according to claim 1, further including the steps of:
representing a help object in the world;
receiving an input from the patient to select the help object; and
providing an indication of the location of the medical objects for a predetermined period of time when the help object is selected.

14. The method according to claim 1, wherein the electronic device includes a touch display and at least one input from the patient is touching the touch display.

15. The method according to claim 1, wherein the electronic device includes a microphone and at least one input from the patient is sound.

16. The method according to claim 1, further including the step of:
displaying information explaining the medical treatment after all of the medical objects have been selected.

17. The method according to claim 16 wherein the information is at least one of a picture, text, a slide show, a sound, a movie or an animation.

18. The method according to claim 1, wherein the medical treatment relates to a burn.

19. The method according to claim 1, wherein the medical treatment is one stage of a medical procedure including a number of medical treatments, further including the step of:
repeating the steps of the method of any one of the preceding claims for at least one other medical treatment stage of the medical procedure.

20. The method according to claim 1, further including the step of:
repeating the steps of claim 1 for all of the medical treatment stages of the medical procedure.

21. A computer readable non-transient memory device storing a computer program comprising instructions for use in an electronic device including a processing unit and associated with the electronic device to perform the computer-implemented method of preparing a patient for medical treatment, wherein the memory device stores the instructions causing the processing unit to carry out the computer-implemented method, the method including the steps of:
representing a world on the display, wherein one or more medical objects related to the medical treatment the patient is preparing to receive are placed in the world represented on the display;
representing one or more obscuring objects in the world, wherein one or more of the medical objects related to the medical treatment are at least partially obscured by one or more of the obscuring objects;
receiving a first input from a patient to perform at least one action to reveal a medical object in the world represented on the display that is at least partially obscured by an obscuring object and performing the action;
receiving a second input from the patient to select the medical object once the medical object used in the medical treatment is revealed in the world represented on the display and selecting the medical object;
providing feedback to the patient to indicate that the medical object has been selected; and
presenting information on the display to explain to the patient the medical treatment to which the one or more selected medical objects relate;
wherein the world is three dimensional and the electronic device includes a motion sensor for detecting motion of the electronic device corresponding to the first input which is received by the motion sensor;
wherein the at least one action performed includes moving the obscuring object represented in the world or changing the viewpoint of the world represented on the display in response to the first input received by the motion sensor, to reveal the medical object in the world that has been at least partially obscured by an obscuring object, for selection of the revealed medical object when the second input is received from the patient.

22. An electronic device including a processing unit and associated memory device for storing a series of instructions for causing the processing unit to carry out a method for using an electronic device having a display to prepare a patient for a medical treatment, the method including the steps of:
representing a world on the display, wherein one or more medical objects related to the medical treatment the patient is preparing to receive are placed in the world represented on the display;
representing one or more obscuring objects in the world, wherein one or more of the medical objects related to the medical treatment are at least partially obscured by one or more of the obscuring objects;
receiving a first input from a patient to perform at least one action to reveal a medical object in the world represented on the display that is at least partially obscured by an obscuring object and performing the action;
receiving a second input from the patient to select the medical object once the medical object used in the medical treatment is revealed in the world represented on the display and selecting the medical object;
providing feedback to the patient to indicate that the medical object has been selected; and
presenting information on the display to explain to the patient the medical treatment to which the one or more selected medical objects relate;
wherein the world is three dimensional and the electronic device includes a motion sensor for detecting motion of the electronic device corresponding to the first input which is received by the motion sensor;
wherein the at least one action performed includes moving the obscuring object represented in the world or changing the viewpoint of the world represented on the display in response to the first input received by the motion sensor, to reveal the medical object in the world that has been at least partially obscured by an obscuring object, for selection of the revealed medical object when the second input is received from the patient.

23. The electronic device according to claim 22, wherein the electronic device is at least one of: a tablet device, has a round shape and a domed shaped back, or a head mountable device.

24. A method for using an electronic device having a display to prepare a patient for a medical treatment, the method including the steps of:
representing a world on the display, wherein one or more medical objects related to the medical treatment the patient is preparing to receive are placed in the world represented on the display;
representing one or more obscuring objects in the world, wherein one or more of the medical objects related to the medical treatment are at least partially obscured by one or more of the obscuring objects;
receiving a first input from a patient to perform at least one action to reveal a medical object in the world represented on the display that is at least partially obscured by an obscuring object and performing the action;
receiving a second input from the patient to select the medical object once the medical object used in the medical treatment is revealed in the world represented on the display and selecting the medical object;
providing feedback to the patient to indicate that the medical object has been selected; and
presenting information on the display to explain to the patient the medical treatment and the selected medical object related to the medical treatment;
wherein the world is three dimensional and the electronic device includes a motion sensor for detecting motion of the electronic device corresponding to the first input which is received by the motion sensor;
wherein presenting information on the display includes displaying one or more of text, a picture, a slide show, a movie or an animation that describe the medical treatment and the selected medical objects;
wherein the at least one action performed includes moving the obscuring object represented in the world or changing the viewpoint of the world represented on the display in response to the first input received by the motion sensor, to reveal the medical object in the world that has been at least partially obscured by an obscuring object, for selection of the revealed medical object when the second input is received from the patient.

* * * * *